United States Patent [19]

Nakanishi

[11] 4,403,956
[45] Sep. 13, 1983

[54] DENTAL HANDPIECE HAVING AN OPTICAL FIBERSCOPE

[75] Inventor: Takasuke Nakanishi, Kanuma, Japan

[73] Assignee: Nakanishi Dental Mfg., Co., Ltd., Kanuma, Japan

[21] Appl. No.: 282,737

[22] Filed: Jul. 13, 1981

[30] Foreign Application Priority Data

Jul. 14, 1980 [JP] Japan ............................ 55-99806[U]

[51] Int. Cl.³ ............................................... A61C 1/00
[52] U.S. Cl. ...................................... 433/29; 433/82; 433/126
[58] Field of Search ...................... 433/29, 32, 82, 126; 285/136; 350/96.22; 362/32

[56] References Cited

U.S. PATENT DOCUMENTS

| | | | |
|---|---|---|---|
| 3,397,457 | 8/1968 | Gosselin | 433/29 |
| 3,893,242 | 7/1975 | Lieb et al. | 433/29 |
| 3,894,338 | 7/1975 | Loge et al. | 433/82 |
| 3,897,134 | 7/1975 | Scrivo et al. | 433/29 |
| 3,936,940 | 2/1976 | Loge | 433/126 |
| 4,080,737 | 3/1978 | Fleer | 433/126 |
| 4,106,796 | 8/1978 | Asztalos et al. | 285/136 |
| 4,217,101 | 8/1980 | Loge | 433/126 |
| 4,260,382 | 4/1981 | Thomson | 433/29 |

FOREIGN PATENT DOCUMENTS 1281054 7/1972 United Kingdom .................. 433/29

Primary Examiner—John J. Wilson
Attorney, Agent, or Firm—Wenderoth, Lind & Ponack

[57] ABSTRACT

A dental handpiece including a powerhead assembly connected to an outer sleeve handle portion in which is located a sleeve bearing, a rotatable, disconnectable connecting means being provided in the sleeve bearing. A first optical fiberscope extends from the front end portion of the powerhead near the dental tool into the front end of the sleeve bearing adjacent to the front end of the connecting means. A thickened fiberscope abuts the rear end of the first fiberscope and extends rearward through the handpiece to a light source. Cavities, passages and pipes are provided in the sleeve bearing and connecting means in order to provide a smooth flow of compressed air, chip air, water and exhaust to or from the powerhead assembly while permitting the sleeve bearing and connecting means to rotate relative to each other about the longitudinal axis of the handpiece.

3 Claims, 6 Drawing Figures

DENTAL HANDPIECE HAVING AN OPTICAL FIBERSCOPE

BACKGROUND OF THE INVENTION

This invention relates to improvements in a dental handpiece having an optical fiberscope which enables a dentist to treat the affected part under illumination.

It has been troublesome for a dentist to treat the affected part under conventional illumination. Some illuminating devices have been proposed, but they are not satisfactory in the viewing and treating of a limited area in the mouth, such as in the treatment of root canals and other fine portions of the tooth structure, such treatment being not only complicated, but also very subtle.

SUMMARY AND OBJECTS OF THE INVENTION

A principal object of this invention is to provide a dental handpiece having an optical fiberscope built in a handle portion whereby the affected part can be treated under illumination by directing the light at or around the dental tool.

Another object of this invention is to provide a dental handpiece having a first fiberscope built in a handle portion and extending into a powerhead assembly, and a second optical fiberscope held in a connecting means and extending into a light source, whereby facing end portions of these optical fiberscopes can be axially brought into direct contact with each other in order to transfer an optical image at or around the affected part to an eye of the dentist.

Another object of this invention is to provide a dental handpiece comprising a holding sleeve, a pneumatic motor mounted at one end of a powerhead assembly to drive a dental tool, and a connecting means releasably and relatively rotatably connected to the other end of the sleeve bearing whereby a handle portion of the dental handpiece can be either removed from the connecting means as a unit assembly or rotatably joined to the connecting means quite easily and quickly.

Another object of this invention is to provide a dental handpiece which can be easily and quickly maintained by oiling and performing repairs.

Another object of this invention is to provide a dental handpiece which can be driven smoothly and quietly.

Still another object of this invention is to provide a dental handpiece which is comparatively simple and small in construction, light in weight and at the same time desirably rigid, strong and durable.

BRIEF DESCRIPTION OF DRAWING

While I have shown in the accompanying drawings, a preferred embodiment of my invention, it should be understood that the same is susceptible of modification and change without departing from the spirit of my invention.

DETAILED DESCRIPTION OF THE PREFERRED EMBODIMENT

Figure 1:
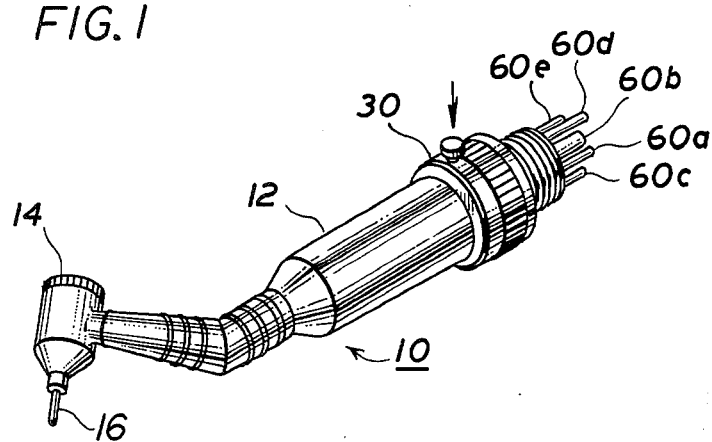
FIG. 1 is a perspective view of the embodiment of the dental handpiece, as contemplated in a preferred embodiment of the present invention.
Figure 2:
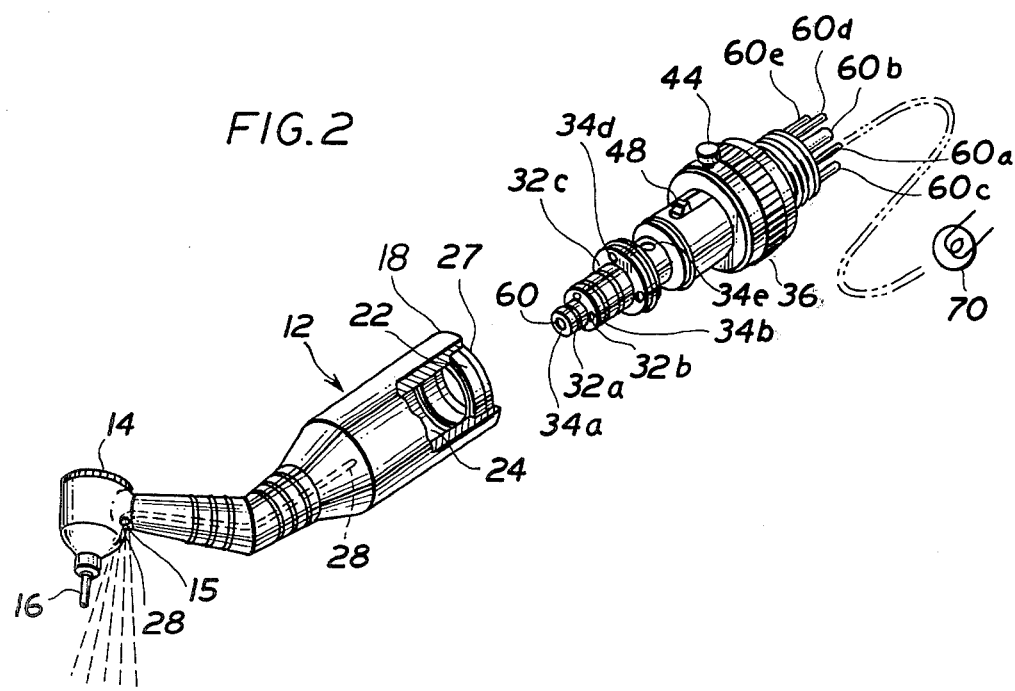
FIG. 2 is a perspective view of the dental handpiece shown in FIG. 1, disassembled into a handle portion and a connecting means, a portion of the handle portion being broken away for clarity.
Figure 3:
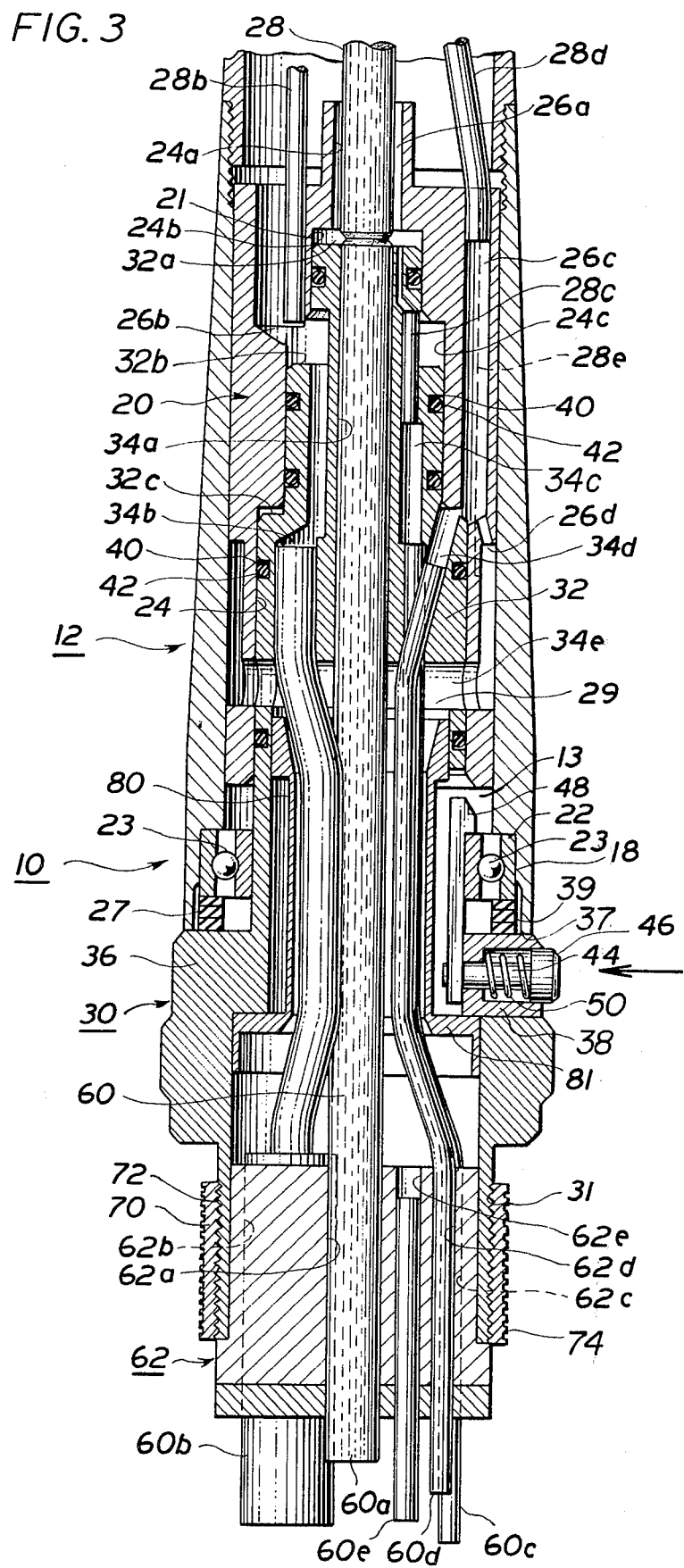
FIG. 3 is a greatly enlarged vertical sectional view of the dental handpiece shown in FIG. 1.

Referring to the drawings, the dental handpiece 10 of the present invention comprises a handle portion 12 and a powerhead assembly 14 which is integrally supported on a front end of the handle portion. At the top end of the powerhead assembly 14 is a pneumatic motor (not shown) which operates, when energized, to rotate at high speed a dental tool shown at 16.

An inwardly recessed slot 18 is formed around an inner circumferential surface of the handle portion 12 near a rear end thereof. A bearing retainer 22 including a plurality of roller bearings 23 therein is inserted into the slot 18 after introducing a sleeve bearing 20 into a hollow 13 of the handle portion 12, the retainer 22 being held in position by a journal packing 27.

Figure 4:
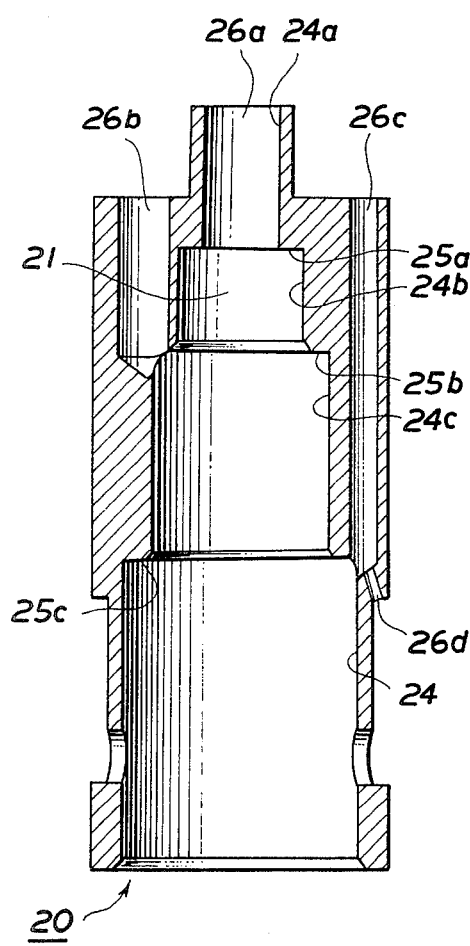
FIG. 4 is an enlarged vertical sectional view of a sleeve bearing to be held in the handle portion.

As shown in FIG. 4, the sleeve bearing 20 is provided with a forwardly reducing cylindrical internal surface 24 including three stepped annular space walls 24a, 24b and 24c which are adjacent and perpendicular to circumferential internal regions 25a, 25b and 25c, respectively. A central passage 26a for a first fiberscope 28 consisting of extremely fine filaments of glass and also forming a duct for introducing chip air is centrally and axially provided to extend through a substantial length of the sleeve bearing 20. In addition, a passage 26b for supplying air under pressure, a passage 26c for supplying water and an exhaust passage 26d are axially provided near and around the central passage 26a and also lengthwise along the sleeve bearing 20.

The diameter of the inner periphery of the passage 26a is larger than that of the first fiberscope 28 so that a duct for introducing chip air is formed between the inner periphery of the passage 26a and the outer periphery of the first fiberscope 28.

The first fiberscope 28 axially penetrates the central passage 26a. The front end of fiberscope 28 extends into the power head assembly 14 and its rear end projects slightly into a central chamber 21 defined by the stepped annular space wall 24a and its adjacent internal region 25a. The front end of the fiberscope 28 protrudes slightly out of an opening 15 in the casing of powerhead assembly 14 adjacent the dental tool 16.

A pipe 28b for supplying air under pressure has a rear end fixedly inserted into the passage 26b and a top end extending into the pneumatic motor within the powerhead assembly 14. A pipe 28c for supplying chip air has a rear end firmly inserted in a passage 34c in plug 32 in sleeve bearing 20, described below and a front end extending into passage 26a. A pipe 28d for supplying water has a rear end fixedly joined into the passage 26c, a front end of which extends into the powerhead assembly 14. Another passage 26e for exhaust is provided axially and in parallel with the passage 26c.

A rear internal portion of the sleeve bearing 20 is so shaped as to form a socket 29 for snugly receiving a connecting means 30. A front portion of the connecting means 30 is so formed into a forwardly reducing cylindrical plug 32 as to fit into the socket 29 of the sleeve bearing 20.

Figure 5:
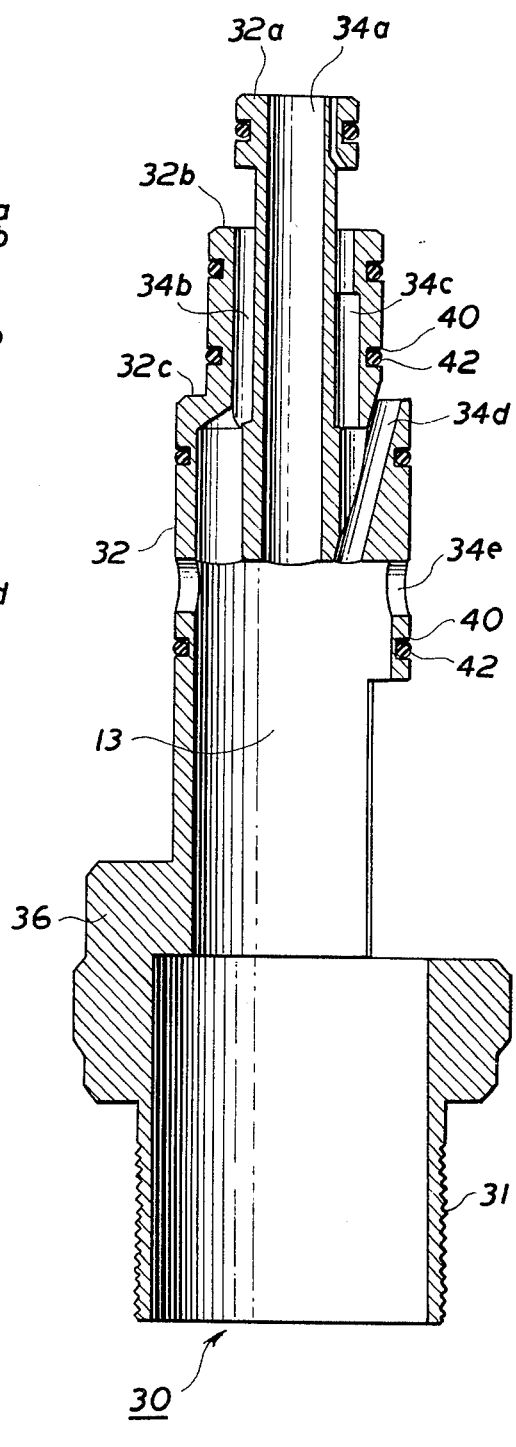
FIG. 5 is an enlarged vertical sectional view of a connecting means to be rotatably journaled in a sleeve bearing.

As shown in FIG. 5, the plug 32 is a forwardly reducing cylinder having a top flat wall 32a and two stepped annular space walls 32b and 32c, each coinciding with the three stepped annular space walls 24a, 24b and 24c respectively.

A central passage 34a for a second fiberscope 60, a side passage 34b for supplying air under pressure and another passage 34c supplying chip air are axially provided to extend through a solid portion of the plug 32 of the connecting means 30. A forwardly outwardly angled passage 34d for water is provided from the hollow 13 to the annular space wall 32c, and a radial exhaust passage 34e is also provided from the hollow 13 to the outer periphery of the plug 32.

When the plug 32 of the connecting means 30 is inserted into the sleeve bearing 20, the top flat wall 32a is brought in close proximity to the stepped annular wall 24a of the sleeve bearing 20, the stepped annular wall 32b is brought in close proximity to the stepped annular wall 24b and the stepped annular wall 32c is brought in close proximity to the stepped annular wall 24c.

The second fiberscope 60 is inserted through the central passage 34a to protrude slightly at its front end portion from the passage 34a so that the rear end of the fiberscope 28 is brought into direct contact with the front end of the fiberscope 60.

A pipe 60b for supplying air under pressure has a front end inserted into the passage 34b, a front end of a pipe 60c supplying chip air is inserted into the passage 34c and a front end of a pipe 60d supplying water is inserted into the angled passage 34d respectively.

A cylindrical hollow chamber 13 is formed within a substantial length of the connecting means 30.

Recessed inwardly from the cylindrical wall of the plug 32, at axially spaced location are circumferencial slots 40, into each of which a separate seal ring 42 is respectively fitted.

A radial socket 37 is provided through the peripheral flange 36 to extend into an axial groove 39 formed through a wall of the plug 32. A cylindrical casing 38 is fixedly put into the radial socket 37. A push-pull rod 44 having a head 46 at its outer end and a right angle hook 48 at its inner end is put into the casing 38 by means of a dead spring 50 to constitute a locking device so that the hook 48 is introduced into the axial groove 39, thus always urging the rod 44 outwardly by the dead spring 50.

A cylindrical hollow support 80 having a radial flange 81 is inserted into the cylindrical hollow chamber 13 in order to support the pipes 60b, 60c and 60d.

Figure 6:
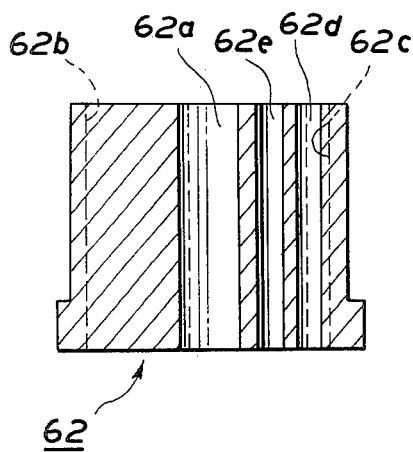
FIG. 6 is an enlarged vertical sectional view of a mounting nut to be inserted into a rear end portion of the connecting means.

As shown in FIG. 6, a hollow mount insert 62 having five axial and parallel openings 62a, 62b, 62c, 62d and 62e is fixedly inserted into a rear end interior of the connecting means 30. The second fiberscope 60 extends through the opening 62a. The pipe 60b supplies air under pressure and extends through the opening 62b. The pipe 60c supplies chip air and extends through the opening 62c. The pipe 60d provides water and extends through the opening 62d. The exhaust pipe 60e is an exhaust pipe and extends through the opening 62e.

An adjustable element or mounting nut 70 with internal threads 72 screws onto the external threads 31 of the connecting means 30, the external threads on nut 70 serving to mount to the handpiece 10 a supply hose of a dental unit.

As explained in the foregoing paragraphs, the plug 32 of the connecting means 30 is rotatably fitted and snugly received in position in the socket 29 of the sleeve bearing 30 so that the top flat wall 32a of the plug is brought in close proximity to the stepped annular wall 24a of the sleeve bearing to bring the rear end portion of the first fiberscope 28 into abutment with the front end portion of the second fiberscope 60, also connecting the chip air pipe 60c with the chip air passage 26a through the pipe 28c and passage 34c. At the same time, the stepped annular wall 32b is brought in close proximity to the stepped annular wall 24b to communicate the compressed air pipe 60b with the pipe 28b inserted in the passage 26b, and the stepped annular wall 32c is brought in close proximity to the stepped annular wall 24c to connect the water supply pipe 60d with the pipe 28d through the passage 26d, also connecting the exhaust pipe 60e to an exhaust pipe 28e in exhaust passage 26e through the radial exhaust passage 34e respectively.

Thus, the plug 32 of the connecting means 30 is airtightly secured into the sleeve bearing 20, allowing circumferential slidable rotation between the plug and the sleeve bearing.

For securing, the plug 32 is introduced into the socket 29 of the sleeve bearing 20 while pushing down with a finger tip the head 46 of the push-pull rod 44 inwardly into the hollow chamber 13 until the top flat wall 32a is brought in close proximity to the innermost stepped annular wall 25a. When the finger is taken off in position, the resiliency of causes the dead spring 50 the push-pull rod 44 to protrude outwardly to engage the hook 48 with a front annular wall of the bearing retainer 22.

Unless the head 46 of the rod 44 is pushed again inwardly, the plug 32 does not separate out of the sleeve bearing 20. In this way, the plug 32 is mounted into the sleeve bearing 20 so as to constitute the dental handpiece 10.

According to the device of this invention, even if the first or second fiberscope is twisted, the desired illumination can be transferred at or around the affected part, and a clear and correct image thereof can be transferred to an eye of a dentist.

While an embodiment of the invention has been described, it is obvious that variations and modifications are possible without departing from the invention. It is desired to cover all such forms of the invention as would be apparent to one skilled in the art, and that come within the scope of the appended claims.

I claim:

1. A dental handpiece for connection to a dental unit comprising:

an outer sleeve having a front end and a rear end;
a powerhead assembly, including means for holding a dental tool and an air-powered turbine wheel, supported on said front end of said outer sleeve, said powerhead assembly having an opening to the exterior thereof adjacent said holding means;
said outer sleeve having an inner circumferential surface defining an internal space;
a sleeve bearing including a circumferentially closed side wall, held in said space of said outer sleeve, said sleeve bearing also having:
a stepped rearwardly increasing diameter cylindrical internal surface including first, second and third stepped cylindrical surfaces and first, second and third radially extending surfaces respectively adjacent said first, second and third stepped cylindrical surfaces, enclosing a stepped cylindrical space, a first central, axial passage having a front and a rear end, said rear end of said first central axial passage opening into said stepped cylindrical space, first and second side passages, each respectively having front and rear ends, near and around said first central passage, the rear ends of said first and second side passages opening axially into said stepped cylindrical space, the front ends of said first and second side passages opening axially into the front end of said outer sleeve, a third side passage opening at one end into the rear end of said first side passage and opening at the other end exteriorly of said side wall, and a radially extending exhaust passage opening to the exterior of said sleeve bearing inside said outer sleeve and to the interior of said stepped cylindrical space rearward of said rear end of said second passage;

a first fiberscope having a front end and a rear end, extending axially through said first central passage, said front end of said fiberscope extending into said powerhead assembly and protruding slightly out of said opening in said powerhead assembly, said rear end of said first fiberscope protruding into said stepped cylindrical space;

a central pipe connecting the front end of said first central passage into the powerhead for supplying chip air thereto;

a first side pipe, connecting said front end of said first side passage to said air powered turbine wheel in said powerhead assembly, for supplying air under pressure thereto;

a second side pipe connecting said front end of said second side passage into said powerhead for supplying water thereto;

a second fiberscope;

means, having a front end and a rear end and including a forwardly reducing cylindrical plug at said front end thereof, for releasably connecting said sleeve to the dental unit, a rear internal portion of said sleeve bearing being so shaped as to form a socket for snugly and axially, rotatably receiving said plug, said connecting means being releasably connected into said sleeve bearing at said rear end thereof; said plug including:

first, second and third coaxial, respectively rearwardly increasing diameter cylindrical walls, a first flat radially extending exterior front wall at the front end of said first cylindrical wall and, second and third radially extending ring-shaped walls at the front ends of said second and third cylindrical walls, respectively, each of said first, second and third radially extending walls respectively confronting said first, second and third radially extending surfaces in respective spaced relation thereto;

said plug having:

a radially large hollow portion defining a hollow space, a second primary central axial passage, opening at opposite ends at the forward end of said hollow sapce and in said first radially extending wall at the forward end of said stepped cylindrical space, for holding said second fiberscope, a fourth side passage having a rear end opening into said hollow space and a front end opening axially in one of said second and third radially extending walls in spaced communication with the rear end of said first side passage, to supply pressurized air thereto, a fifth side passage having a rear end opening onto said hollow space and a front end opening axially in said first radially extending wall into the forward end of said stepped cylindrical space for supplying chip air thereto, a sixth forwardly and radially outwardly angled side passage having a rear end opening into said hollow space and a front end opening through the other of said second and third radially extending walls into spaced communication with the rear end of said second side passage, and a radially extending second exhaust passage coinciding with said first exhaust passage and opening to the exterior of said sleeve bearing and said rear end of said third side passage through said first exhaust passage and to the interior of said hollow space, for exhausting water and pressurized air;

said second fiberscope extending through said second central passage and having a front end abutting said rear end of said first fiberscope;

a mount insert having five axially extending insert passages, fitted to said connecting means rearward of said hollow space;

four insert pipes, three of said four insert pipes and the rear end of said second fiberscope respectively extending through four of said five insert passages, through said hollow space and into said fourth, fifth and sixth side passages and said second central passage, respectively; and a fifth insert pipe extending into the fifth of said five insert passages for exhausting water and pressurized air from said second exhaust passage; whereby fluid and light communication between said five insert pipes and said powerhead assembly is maintained irrespective of the axial rotation of said plug relative to said sleeve bearing, the front end face of said second fiberscope being slidingly rotatable against the rear end face of said first fiberscope.

2. A dental handpiece as in claim 1, wherein said outer sleeve has an interior forwardly and radially outwardly recessed slot around said inner circumferential surface near said rear end of said outer sleeve; said dental handpiece further comprising ball bearing means for rotatably mounting said connection means into said sleeve bearing and said outer sleeve.

3. A dental handpiece as in claim 1 or claim 2, further comprising a hollow cylindrical support having a radial flange inserted into said hollow space for supporting said four of said five insert pipes within said connection means.

* * * * *